United States Patent [19]

Tanaka et al.

[11] Patent Number: 4,912,388
[45] Date of Patent: Mar. 27, 1990

[54] DRIVE CONTROL DEVICE OPERATING A DRIVE MECHANISM

[75] Inventors: Shinya Tanaka, Tokyo; Yukitsugu Nakamura, Sagamihara, both of Japan

[73] Assignee: Canon Kabushiki Kaisha, Tokyo, Japan

[21] Appl. No.: 217,077

[22] Filed: Jul. 8, 1988

Related U.S. Application Data

[63] Continuation of Ser. No. 890,750, Jul. 30, 1986, abandoned.

[30] Foreign Application Priority Data

Aug. 2, 1985 [JP] Japan .................. 60-171496
Jan. 18, 1986 [JP] Japan .................... 61-8681

[51] Int. Cl.$^4$ .............................. G05B 19/40
[52] U.S. Cl. .............................. 318/640; 318/603; 250/221; 73/606; 350/521; 350/530
[58] Field of Search .............. 318/460, 603, 685, 608, 318/600, 601, 640; 350/521, 530, 523, 515, 519, 520, 526; 250/221, 229, 204; 73/606, 614, 609, 615; 364/513.5; 381/43

[56] References Cited

U.S. PATENT DOCUMENTS

| | | | |
|---|---|---|---|
| 2,545,727 | 3/1951 | Dooley | 361/179 |
| 3,673,327 | 6/1972 | Johnson et al. | 250/221 X |
| 4,000,419 | 12/1976 | Crost | 350/538 X |
| 4,128,944 | 12/1978 | Stanton | 350/515 |
| 4,206,990 | 6/1980 | Imura | 354/266 X |
| 4,254,333 | 3/1981 | Bergstrom | 250/221 |
| 4,286,849 | 9/1981 | Uchidoi | 354/486 X |
| 4,305,006 | 12/1981 | Walthall | 307/117 X |
| 4,328,713 | 5/1982 | Lund | 350/515 X |
| 4,340,813 | 7/1982 | Sauer | 250/221 |
| 4,388,495 | 6/1983 | Hitchcock | 381/43 |
| 4,420,979 | 12/1983 | Momii et al. | 73/606 X |
| 4,430,897 | 2/1984 | Quate | 73/606 |
| 4,450,545 | 5/1984 | Kishi | 307/117 X |
| 4,461,560 | 7/1984 | Yoshino | 354/475 X |
| 4,462,080 | 7/1984 | Johnstone et al. | 364/513.5 |
| 4,465,355 | 8/1984 | Murakami | 354/475 |
| 4,531,816 | 7/1985 | Baumgartel | 350/521 |
| 4,567,767 | 2/1986 | Quate et al. | 73/606 |
| 4,577,141 | 3/1986 | Saiki et al. | 318/603 X |
| 4,593,403 | 6/1986 | Kishi et al. | 364/513.5 |
| 4,618,934 | 10/1986 | Nagase | 73/620 X |
| 4,628,496 | 12/1986 | Lee | 307/117 X |
| 4,639,587 | 1/1987 | Chadwick et al. | 250/204 X |
| 4,653,878 | 3/1987 | Nakasato | 350/520 |
| 4,674,333 | 6/1987 | Jindo et al. | 73/606 |
| 4,682,091 | 7/1987 | Krewalk et al. | 318/603 X |
| 4,695,137 | 9/1987 | Jorgens et al. | 350/521 |
| 4,716,992 | 1/1988 | Kunii | 250/221 X |
| 4,749,270 | 6/1988 | Endo et al. | 350/530 X |

FOREIGN PATENT DOCUMENTS

| | | | |
|---|---|---|---|
| 3147836 | 7/1982 | Fed. Rep. of Germany | 350/507 |
| 53-134182 | 11/1978 | Japan | 318/565 |
| 45363 | 3/1980 | Japan . | |
| 57-201906 | 12/1982 | Japan | 318/565 |
| 58-132804 | 8/1983 | Japan | 318/565 |
| 164057 | 9/1984 | Japan . | |
| 59-183412 | 10/1984 | Japan | 318/565 |
| WO86/01953 | 3/1986 | World Int. Prop. O. | 307/117 |

OTHER PUBLICATIONS

Ro, Bentsu: "Application of Fourier Transform Deconvolution", Doctorate Dissertation, Marquette University, Milwaukee, Wis., 1982, pp. 30, 154, 155.

*Primary Examiner*—William M. Shoop, Jr.
*Assistant Examiner*—Paul Ip
*Attorney, Agent, or Firm*—Fitzpatrick, Cella, Harper & Scinto

[57] ABSTRACT

A drive control device has a driving switch for remotely-operating a plurality of drive mechanisms, and a transmission device for transmitting to the operator the kind of a drive mechanism which is about to be driven, before the driving by the driving switch.

21 Claims, 7 Drawing Sheets

DRIVE CONTROL DEVICE OPERATING A DRIVE MECHANISM

This application is a continuation-in-part of application Ser. No. 890,750 filed July 30, 1986 now abandoned.

BACKGROUND OF THE INVENTION

1. Field of the Invention

This invention relates to a drive control device for use chiefly in the field of medical science, and more particularly to a drive control device which operates a drive mechanism for effecting various positional adjustments, for example, in a stereoscopic microscope.

2. Related Background Art

Stereoscopic microscopes are widely used for medical treatments such as operations and examinations, for researches and for the industries. These microscopes are useful to improve the precision and safety of the treatment.

Usually, a stereoscopic microscope is comprised of a microscope body comprising a combination of a binocular stereoscopic microscope and an illuminating device, and a stage for supporting the microscope body and freely effecting positional adjustment. FIG. 1 of the accompanying drawings shows the general construction of a stereoscopic microscope of the conventional popular floor installation type having a binocular microscope comprising right and left independent observation optical systems Ma and Mb and used chiefly as a microscope for operation. Affixed strut 2 is provided on a stand 1, and a movable arm 3 is mounted on the fixed strut 2 for rotation and sliding movement in vertical direction indicated by bilateral arrow A. An S-Y fine movement device 4 containing therein a drive mechanism for fine movement in X-Y directions indicated by arrows B and C is rotatably suspended from the movable arm 3, and a microscope head 5 is connected to the lower end of the X-Y fine movement device 4 so as to be slidable in vertical direction indicated by bilateral arrow D by a vertically moving device. Also, a foot switch bed 6 is connected to the stand 1 by an electric cord, and a switch 7 for X-Y direction fine movement, a switch 8 for vertical coarse movement, a switch 9 for zooming and a switch 10 for focusing are provided on the foot switch bed 6.

The vertical coarse movement and X-Y direction fine movement indicated by arrows A-D and the zooming and focusing of the optical system are accomplished by an electric motor, and the control of the electric motor is accomplished by a foot properly stepping on the switches 7–10 arranged on the foot switch bed 6. However, such a stepping operation makes the positions of the switches difficult to know, involves the danger of malfunctioning and causes the reduced safety of operations or the like.

As a method of solving tee above-noted problem, an attempt has been made to control all the driving of the above-described various devices by means of voice, but in this method, the drive mechanism is directly controlled by voice and therefore, not only fine adjustment of each drive cannot be freely accomplished by the operator, but also there are many kinds of voice to be recognized and thus, the apparatus becomes complicated and there is the possibility of malfunctioning, so this method is not yet put into practical use.

To overcome the disadvantage peculiar to the foot switch, a so-called hand controller is also known in which a switch board having a number of switch buttons arranged on or closely adjacent t the surface of the microscope head and it is operated by the operator actuating it with his finger tip, but in this case, the operator's finger tip directly touches the switch buttons and therefore, the problem of disinfection or sterilization arises. For this reason, it has been conceived to gas-disinfect the entire device having the switch buttons each time it is used, or to attach disinfected rubber caps or the like to the switch buttons, or to operate the device with a disinfecting cover attached thereto, but these works are cumbersome and moreover cannot be said to be sufficiently germfree. Further, the manual actuation of the switch buttons somewhat oscillates the microscope head to make it difficult to accomplish sufficiently precise fine adjustment. Also, since the operator operates the apparatus while looking into the microscope, it is difficult for the operator to discriminate between the positions of the numerous switch buttons, and the risk of malfunctioning is also great.

SUMMARY OF THE INVENTION

It is an object of the present invention to provide a drive control device designed to cause the operator to recognize in advance the substance of the operation of a switch which controls a plurality of drive mechanisms, thereby eliminating the risk of malfunctioning.

It is also an object of the present invention to provide a drive control device which is simple to operate and eliminates the problem of disinfection or sterilization.

DESCRIPTION OF THE PREFERRED EMBODIMENTS

Figure 1:
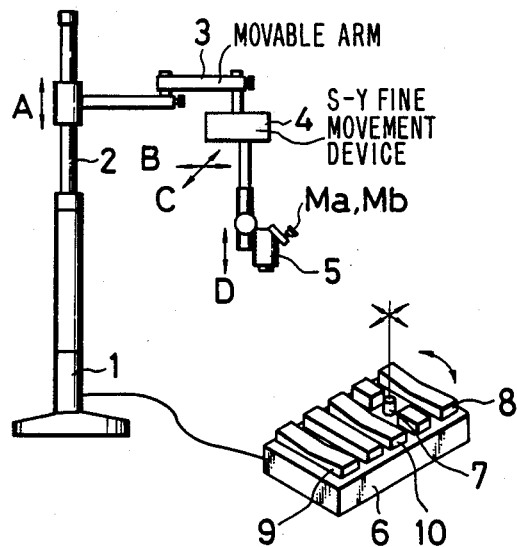
FIG. 1 shows the whole of a microscope for operation according to the prior art.
Figure 2A:
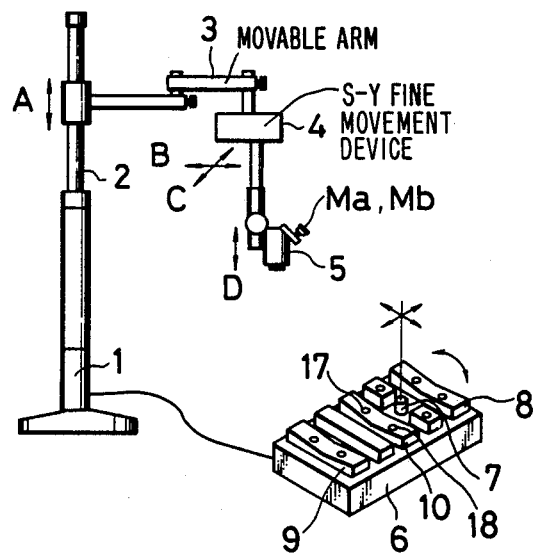
FIGS. 2 (A) and 2(B) show the whole of a first embodiment of the present invention and the circuit construction of the essential portions thereof, respectively.
Figure 2B:
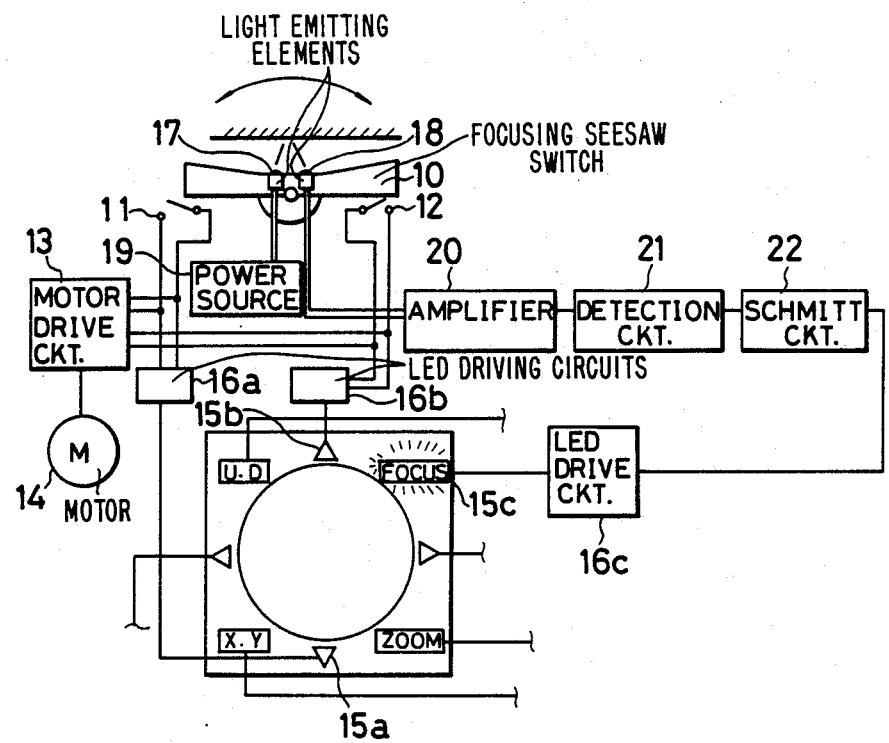

Referring to FIG. 2(A) which shows the basic construction of a first embodiment of the present invention, reference characters similar to those in FIG. 1 designate similar members. In FIG. 2(B), a case where the present invention is applied to a focusing witch 10 is exemplarily shown, but the other foot switches 7–9 are also constructed similarly.

Contacts 11 and 12 are disposed near the opposite ends of the underside of the focusing seesaw switch 10, and a motor 14 is connected to these contacts 11 and 12 through a motor drive circuit 13. Further, an LED driving circuit 16a for driving an LED 15a disposed on the focal plane of the eyepiece of a microscope is connected to the contact 11 and an LED driving circuit 16b for driving a LED 15b is connected to the contact 12. Also, a reflection type photo proximity switch comprising a light-emitting element 17 and a light-receiving element 18 is provided at the center of the seesaw switch 10, a power source 19 is connected to the light-emitting element 17, and an amplifying circuit 20, a detecting circuit 21, a Schmitt trigger circuit 22 and an LED driving circuit 16c are successively connected to the light-receiving element 18. The LED driving circuit 16c is adapted to drive an LED 15c on the focal plane of the eyepiece.

FIGS. 3(A) and 3(B) show the construction of a light emitting display device on the focal plane of the eyepiece. In these Figures, only the members corresponding to the LED 15b are shown. A display device 28 comprising a base plate 25, a field stop 26 and a vinyl sheet 27 shown in FIG. 3(A) layered integrally with one another is mounted at the focus position of the eyepiece 24 provided in the eyepiece housing 23 of the microscope. The display LED 15b is mounted on the base plate 25, an opening 26a corresponding to the LED 15b is formed in the field stop 26, and a transmission pattern switchable for display is formed on the vinyl sheet 27 so that the light emitted from the LED 15b may pass through the opening 26a and illuminate the transmission pattern.

In the microscope for operation constructed as described above, when the examiner brings his foot close to the focusing seesaw switch 10 to adjust the focus of the microscope, the light from the light-emitting element 17 is diffused and reflected by the examiner's foot and detected by he light-receiving element 18. The output signal of the light-receiving element 18 is input to the LED driving circuit 16c via the amplifying circuit 20, the detecting circuit 21 and the Schmitt trigger circuit 22, and the LED 15c on the base plate 25 is turned on and the transmission pattern 27a displaying characters such as FOCUS on the vinyl sheet 27 is illuminated and thus, the examiner O can observe the transmission pattern 27a with the image E' of the region E to be examined by an objective, in the field of view of the microscope, and can observe the correctness or incorrectness of the selection of the switch 10 before operation.

When the foot of the examiner O steps on the seesaw switch 10 in any direction after the confirmation of the correctness or incorrectness, the contact 11 or 12 is contacted by the switch 10 and the signal thereof passes through the motor driving circuit 13 as in the conventional apparatus and revolves the motor 14 in a direction of revolution corresponding to the direction of focusing corresponding to the contact 11 or 12, thereby driving a focusing mechanism. At the same time, the contact signal of the contact 11 or 12 is input to the LED driving circuit 16a or 16b to turn on the LED 15a or 15b, and the examiner O can observe the transmission pattern 27b or 27c such as an arrow indicating the direction of operation, together with the image E' of the region E to be examined, thus confirming whether a correct operation is actually performed.

Such a mechanism shown in FIGS. 2 and 3(A) and 3(B) is similarly constructed for a switch 7 for fine movement in X-Y direction, a switch 8 for coarse movement in vertical direction and a zooming switch 9. Accordingly, when the examiner brings his foot close to the zooming seesaw switch 9 to vary the magnification of the microscope, the characters 200M designated by 27d are displayed in the field of view of the microscope in the same manner as in the case of focusing. When the seesaw switch 9 is stepped on to drive the zoom mechanism, an arrow or the like corresponding to that direction is displayed by emitted light. The display by emitted light is effected similarly with respect also to the other driving devices, whereby the confirmation before and during the operation of the driving devices can be obtained.

In the present embodiment, the correctness or incorrectness of the switch selection before the operation of the driving devices can be confirmed in this manner and also the state of driving of the apparatus can be confirmed by the light emission display of an arrow or the like and further, the position of the examiner's foot during operation can always be confirmed and therefore, the risk of malfunctioning can be remarkably reduced.

Detecting means such as a limit switch for detecting the arrival of the above-described various driving mechanisms at the limit position of the movement range may be incorporated so that when the limit position has been reached, for example, an arrow or the like may be turned on and off to thereby inform the examiner that the driving mechanisms will not move any more even if the examiner continues to step on the foot switch being operated, whereby useless operation can be omitted and the operability can be improved.

Also, besides the system using the reflection type proximity switch of the present embodiment, the means for detecting in advance what is to be driven by the selected switch may be such that for example, a two-stroke switch is used as the foot switch so that what is to be driven by that switch is detected in a first stroke and when the switch is further stepped on to a second stroke, the driving device operates actually.

Further, in the above-described embodiment, design is made such that the substance of the switch selection is displayed by emitted light in the field of view of the microscope, but the LED driving circuit 16c, etc. of FIG. 2 may be replaced by a voice producing circuit so that the name or the like of the selected switch may be transmitted to the examiner by voice. In the previous embodiment, the display element is provided in the microscope and therefore the construction is somewhat complicated, but by using voice as the transmitting means, it becomes possible to make the circuit independent and thus, simplify the construction.

Figure 4:
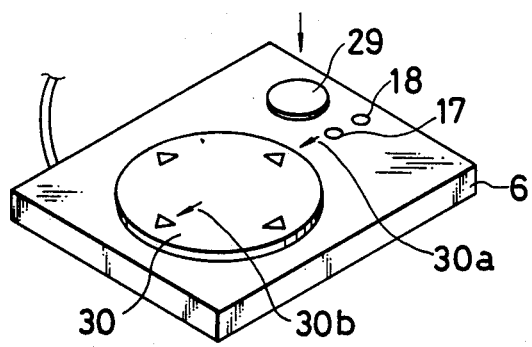
FIG. 4 is a perspective view of a foot switch in a second embodiment.

It is also possible to simplify the switches on a foot switch bed 6. FIG. 4 shows a second embodiment, and more particularly shows the simplified construction of the switches on the foot switch bed 6. A mode changing-over momentary switch 29 is installed on the foot switch bed 6, proximity switches 17 and 18 are disposed near the momentary switch 29, and a drive switch 30 formed by two pairs of seesaw switches is provided on the substantially central portion of the foot switch bed 6.

When the apparatus is to be driven, what region of the apparatus should be driven is first selected by the mode changing-over switch 29. At that time, the examiner's foot is detected by the proximity switches 17 and 18 similar in construction to those of FIG. 2, and the light emission display of FOCUS, for example, of the focusing which is the previous mode is turned on and off in the field of view of the microscope, and by this turn-on-and-off, the examiner can confirm that his foot lies on the mode changing-over switch 29. But if the shapes or sizes of the mode changing-over switch 29 and operating switch 30 are made greatly different from each other as shown in FIG. 4, discrimination between these two switches is easy and therefore, the proximity switches 17 and 18 can be eliminated. Each time the mode changing-over switch 29 is stepped on once, the function mode is changed over, for example, to zooming, vertical coarse movement, focusing and XY fine movement in succession, and in the field of view of the microscope, the selected mode is displayed by emitted light similarly to the light emission display shown in FIG. 2 so that an appropriate mode can be selected. For example, when the change-over mode is the zooming mode at first, ZOOM is displayed by emitted light in the field of view, and only a pair of seesaw switches, e.g., 30a and 30b, of the foot switch becomes effective and, by operating the foot switch 30 toward 30a or 30b, the direction of driving is displayed by emitted light in the field of view and at the same time, the zoom lens system of the microscope is driven correspondingly to the direction of operation and thus, the observation magnification of the microscope is varied.

When the operation of focusing is to be effected, the operator moves his foot to the mode changing-over switch 29. When the mode changing-over switch 29 is stepped on thereafter, the mode changes over to the vertical movement mode, and when the mode changing-over switch 29 is further stepped on, the mode changes over to the focusing mode and the displaying the field of view changes to FOCUS. At this time, the turn-on-and-off of the display of FOCUS continues in order to indicate that the changing-over switch 29 is being operated. When in this state, the operator moves his foot onto the operating switch 30, the turn-on-and-off of the display of FOCUS stops and FOCUS is displayed by normal emitted light. The focus of the microscope can be adjusted by suitably operating the operating switch 30.

Figure 5:
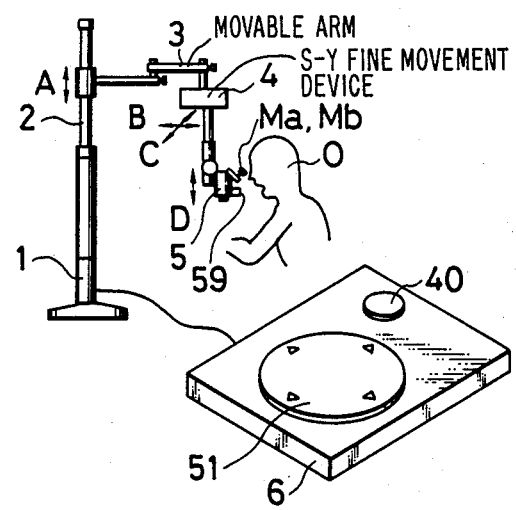
FIG. 5 shows the whole of a microscope for operation according to a third embodiment which uses voice.

FIG. 5 is a pictorial view showing the construction of a third embodiment of the present invention. This embodiment is a microscope for operation in which the mode change-over by the mode changing-over switch in the embodiment of FIG. 4 is replaced by the mode change-over by voice input. Reference numeral 51 designates a multifunction switch having four contacts similar to the member 30 of FIG. 4. A microphone 59 for inputting the voice produced by the operator O to a voice recognizing circuit contained in the stand 1 is provided on the microscope head 5. Denoted by 40 is a foot switch for disabling voice inputting from being effected as will be described later when it is unnecessary.

Figure 6:
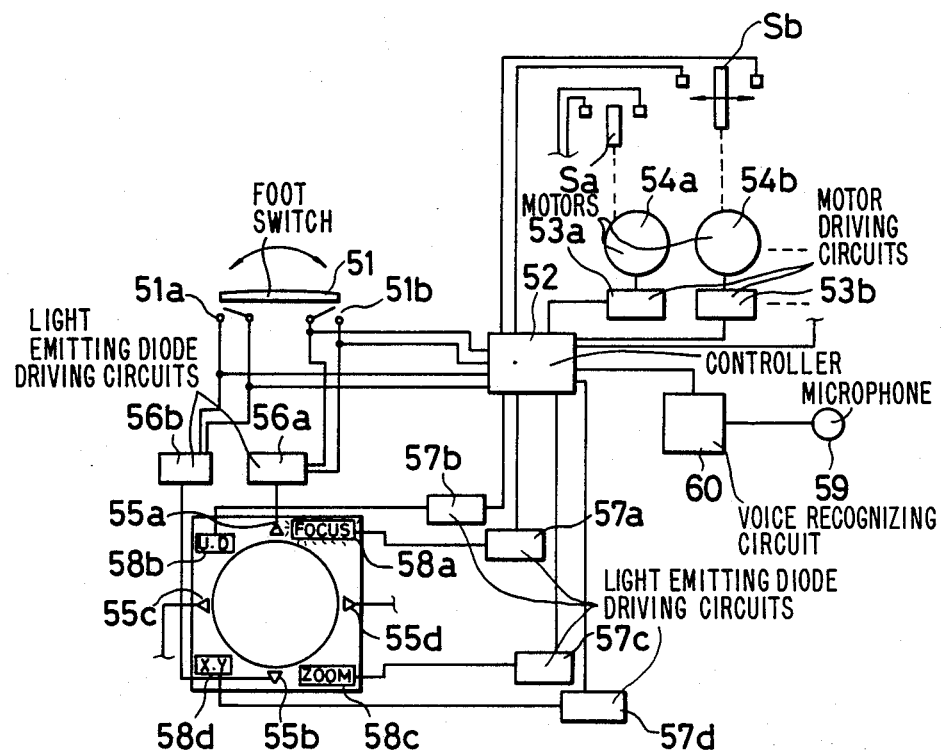
FIG. 6 shows the circuit construction of the essential portions of the FIG. 5 embodiment.

FIG. 6 shows the basic circuit construction of the essential portions of the FIG. 5 embodiment. The foot switch 51 has four contacts 51a–51d (of which the contacts 51c and 51d are not shown). These contacts 51a–51d are input to a controller 52, the output of which is connected to motor driving circuits 53a–53d (of which the motor driving circuits 53c and 53d are not shown). Also, motors 54a–54d (of which the motors 54c and 54d are not shown) for effecting various drives circuits 53a–53d, respectively, so that various drives of the apparatus can be effected through the controller 52 in response to the input of the foot switch 51. Further, light-emitting diode driving circuits 56a–56d (of which the driving circuits 56c and 56d are not shown) for driving light-emitting diodes 55a–55d for indicating the direction of operation which are disposed on the focal plane of the eyepiece of the microscope body 5 are connected to the contacts 51a–51d of the foot switch 51. Also, the output of the controller 52 is connected to light-emitting diodes 58a–58d disposed on the focal plane of the microscope body 5 for displaying the voice recognition, through light-emitting diode driving circuits 57a–57d. A voice input microphone 59 is contained in the microscope body 5, and the input signal thereof is recognized by a voice recognizing circuit 60, the output of which is connected to the controller 52.

The voices recognized by the voice recognizing circuit 60 are the names of the various drives of the apparatus such as "FOCUS", "ZOOM", "UP-DOWN" and "XY", and when such voice recognition information is input from the voice recognizing circuit 60 to the controller 52, the controller 52 connects the switch contacts 51a–51d of the multifunction switch 51 to the motor driving circuits 53a–53d corresponding to the inputs thereof and allots them to the corresponding modes and also provides an output signal to the corresponding one of the light-emitting diode driving circuits 57a–57d and causes the light-emitting diodes 58a–58d which effect the display corresponding to the voice input on the focal plane of the microscope body 5 to emit light.

Figure 3:
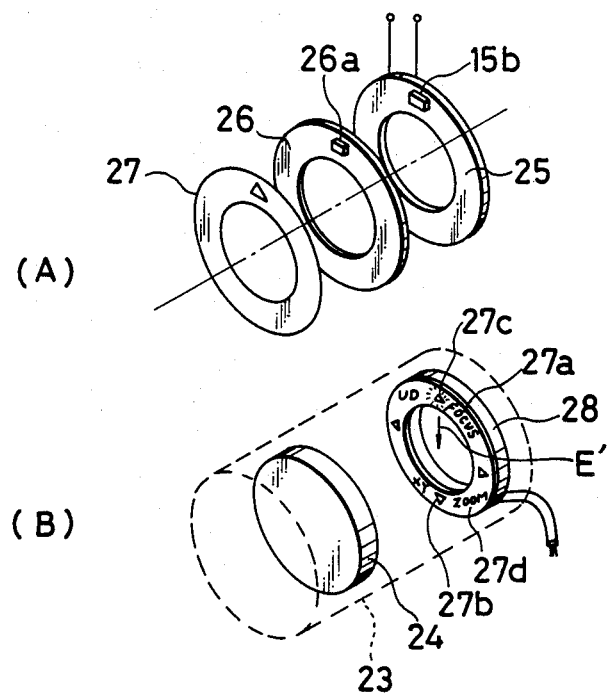
FIGS. 3(A) and 3(B) are perspective views of a display portion.

In the microscope for operation constructed as described above, when the operator O utters "FOCUS" toward the microphone 59 to adjust, or example, the focus of the microscope, the voice recognizing circuit 60 judges the voice signal of the microphone 59 and inputs the information to the controller 52, which in response to that signal puts out a signal to the light-emitting diode driving circuit 57a to cause the light-emitting diode 58a to emit light and also cause the foot switch to correspond to the focus driving motor driving circuit 53a. By the light emission of the light-emitting diode 58a, the transmission pattern 27a on the vinyl sheet 27 displaying the characters "FOCUS" as shown in FIG. 3 is illuminated. The operator O can observe, in the field of view of the microscope body 5, the transmission pattern 27a together with the image of the region to be examined formed by the objective, and thus can confirm the correctness or incorrectness of the selection of the mode before the operation is started.

When after the confirmation of the correctness or incorrectness, the foot of the operator O steps on the foot switch toward the contact 51a or 51b, the contact 51a or 51b is contacted by the foot switch and the signal thereof passes through the controller 52 and the motor driving circuit 53a and revolves the motor 54a in a direction of revolution corresponding to the focusing direction conforming to the contact 51a or 51b, whereby the motor 54a drives the focusing mechanism. At the same time, the contact signal by the contact 51a or 51b is input to the light-emitting diode driving circuit 56a or 56b, which thus turns on the light-emitting diode 55a or 55b, and the operator O can observe the transmission pattern 27a which is an arrow, and can confirm whether a correct operation is being performed actually.

Such an operation is similarly performed with respect also to the fine movement in X-Y direction, the coarse movement in vertical direction and the zooming. Accordingly, when the operator utters "ZOOM" to vary, for example, the observation magnification of the microscope, the pattern of "ZOOM" is displayed by emitted light in the field of view of the microscope as in the case of focusing, and the foot switch 51 becomes connected to the motor driving circuit 53b for driving the zoom mechanism. When the operator O steps on the foot switch 51 and the motor 54b for zooming is driven, an arrow corresponding to that direction is displayed by emitted light. The light emission display is effected likewise with regard also to the other driving devices and confirmation of the operation mode can be obtained before the operation of the driving devices.

Detecting means such as limit switches Sa and Sb for detecting the arrival of the respective driving mechanisms at the limit position of the movement range are incorporated, and when the limit position has been reached, the limit switches Sa and Sb are struck and turn on and off, for example, the arrow or the like, whereby the operator is informed that the driving mechanism will not be moved any more even if the operator continues to step on the foot switch 51 during the operation, and thus any useless operation is eliminated and the operability is further improved.

Figure 7:
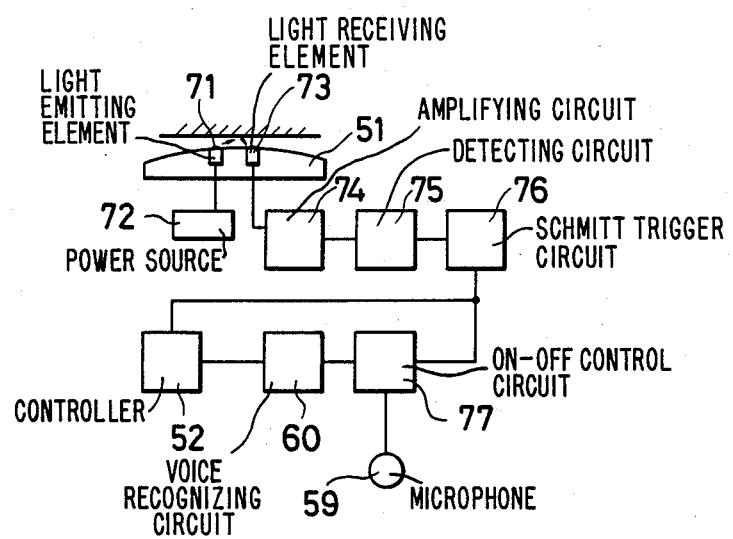
FIG. 7 shows the construction of a fourth embodiment.

Now, with regard to a voice input, to eliminate the risk of the misjudgement thereof in particular, it is desirable to provide such a foot switch 40 as shown in FIG. 5 that voice inputting cannot be effected when it is unnecessary, and it is effective in respect of operability to provide such switch 40 near the multifunction foot switch 51, and further, it is considered to be best that the switch 40 is contained as a noncontact type switch in the foot switch 51, and the construction thereof is shown as a fourth embodiment in FIG. 7.

Designated by 71 in FIG. 7 is a light-emitting element. A power source 72 is connected to the light-emitting element 71, and there is also provided a light-receiving element 73 for receiving the reflected light of the light-emitting element 71. When the operator O brings his foot close to the foot switch 51 to adjust, for example, the microscope, the light from the light-emitting element 71 is diffused and reflected by the foot of the operator O and detected by the light-receiving element 73. An amplifying circuit 74, a detecting circuit 75 and a Schmitt trigger circuit 76 are connected in series with the light-receiving element 73. Further, the output of the Schmitt trigger circuit 76 is connected to an ON-OFF control circuit 77, to which is connected a voice microphone 59.

Accordingly, the output signal of the light-receiving element 73 is input to the voice input ON-OFF control circuit 77 via the amplifying circuit 74, the detecting circuit 75 and the Schmitt trigger circuit 76, thus switching on the voice input microphone 59. With such a construction unless the operator O places his foot on the foot switch 51, the voice input circuit is in its OFF state and therefore, the operator can do his work without being conscious o the presence of the voice input device.

Further, if, a shown in FIG. 7, design is made such that the output of the Schmitt trigger circuit 76 is input to the controller 52 and the light-emitting diode driving circuits 57a–57d for displaying the operation mode of the foot switch 51 are switched on or off by that signal, various displays will be effected in the microscope body 5 only when necessary, and this is more effective.

The above-described embodiment using voice can eliminate the problem that in the conventional stepping operation, the position of the switch is difficult to know and this involves the danger of malfunctioning and causes a reduction in the safety of operation, as well as the problem that in the operation wherein control is all effected by voice, the driving mechanism is directly controlled by voice and therefore not only fine adjustment of each drive cannot be freely accomplished by the operator, but also there are many kinds of voice to be recognized and this complicates the apparatus and gives rise to the possibility of malfunctioning.

Figure 8A:
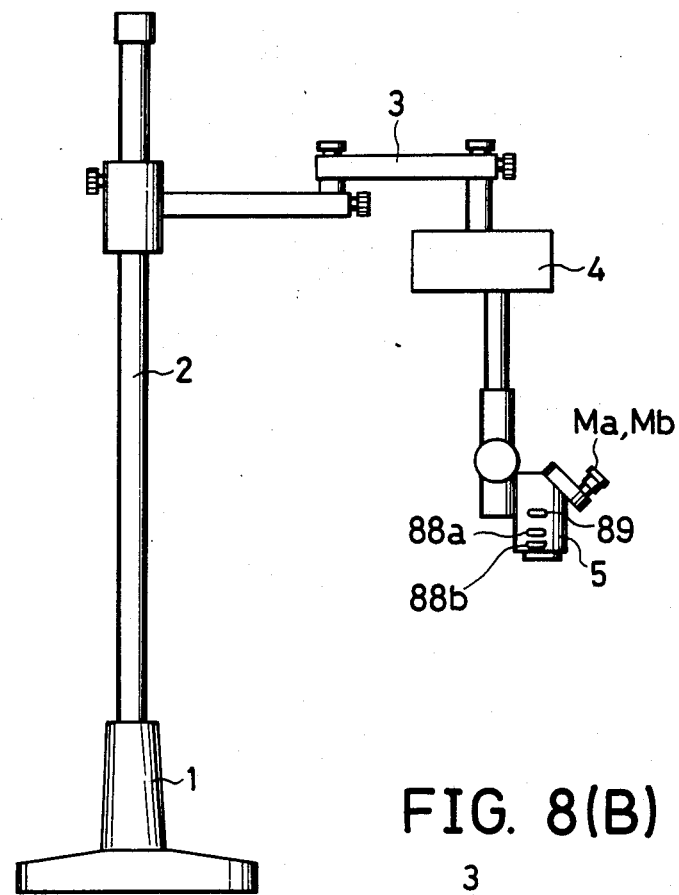
FIG. 8(A) shows the construction of a fifth embodiment.
Figure 8B:
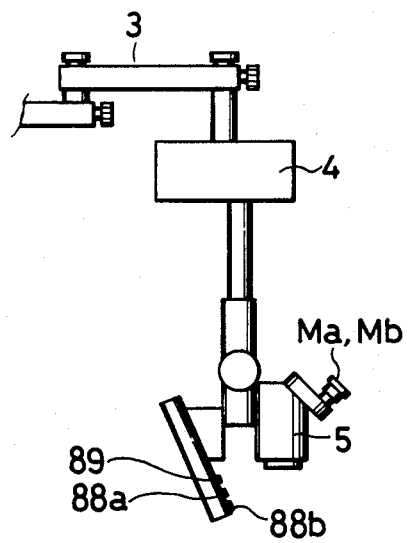
FIG. 8(B) shows a modification thereof.
Figure 9:
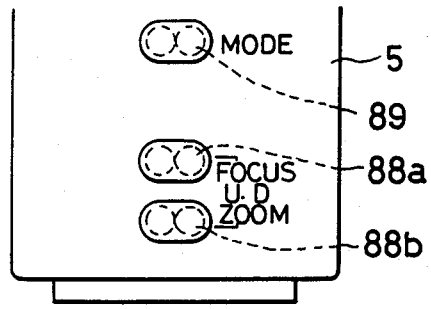
FIG. 9 shows a photoswitch on which a non-contact type mode changing-over switch is installed.
Figure 10:
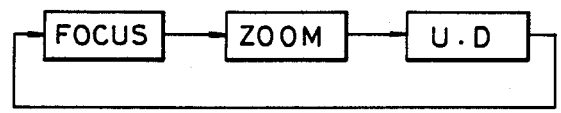
FIG. 10 illustrates the mode change-over.
Figure 11:
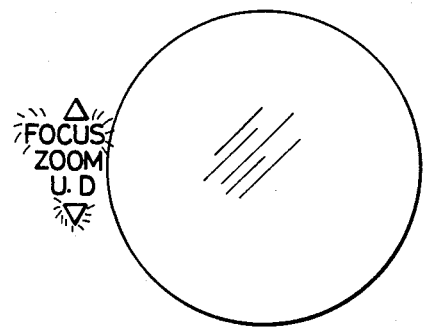
FIG. 11 illustrates the mode display in the operator's field of view.

FIGS. 8(A) and 8(B) show a fifth embodiment and a modification thereof, respectively. While the above-described embodiment has been shown as being applied to a foot switch, the present embodiment is shown as being applied to a so-called hand controller in which a switch board is provided on the surface of the microscope head On a side of the microscope head 5, there are mounted non-contact type switches using such photoelectric reflection type photoswitches as shown in FIG. 9. That is, in FIG. 9, a pair of photoswitches 88a and 88b for focusing, zooming and vertical movement operation and a mode changing-over photoswitch 89 are provided on the surface of the microscope head 5. Each time the operator brings his finger tip or a scalpel close to the mode changing-over photoswitch 89, the function mode is changed over to focusing (FOCUS), zooming (ZOOM), up-down (U.D.) focus, ... in succession, as shown in FIG. 10, and in the field of view of the eyepiece, a selected mode is displayed by emitted light as shown in FIG. 11 so that an appropriate mode can be selected. If not only the selected mode but also the arrow or the like indicting the direction of operation is displayed in the field of view, the apparatus will become easier to use and the possibility of malfunctioning will decrease The display in the field of view is not restricted to this example of the display, but can also be applied to other examples of the driving.

Even if the operator releases his finger tip or the like from the mode hanging-over photoswitch, this selected mode is maintained as it is and the photoswitches 88a and 88b function as the operating switches during that selected mode. For example, when the mode changing-over photoswitch 89 is in the zooming mode at first, "ZOOM" is displayed by emitted light in the field of view, and when the operator brings his finger tip or the like close to the photoswitch 88a or 88b, the zoom lens is operated to the wide angle side or the narrow angle side by the drive of an electric motor.

Next, where the focusing operation is to be performed, when the operator brings his finger tip or the like close to the mode changing-over photoswitch 89 once, the mode changes over to the up-down mode, and when the operator brings his finger tip or the like close to the mode changing-over photoswitch 89 once more, the mode changes over to the focusing mode and the display in the field of view changes to "FOCUS". In this state, the operator can perform the focusing operation by bringing his finger tip or the like close to the photoswitch 88a or 88b.

In FIG. 10, the modes are arranged in the order of FOCUS, ZOOM and U.D., but of course, other arrangements may be adopted and XY direction fine movement operation can be added. But if the number of selected modes is too great, too long a time will be required for the mode selection.

Further, in the above-described embodiment, the mode changing-over photoswitch 89 is provided discretely, but the pair of photoswitches 88a and 88b may be made to perform also the function of the mode changing-over photoswitch. That is, the mode changing-over photoswitch 89 could be eliminated if setting is made such that mode change-over is effected when the operator brings his two fingers or his palm close to the two photoswitches 88a and 88b so that reflected light enters the light-receiving elements of the photoswitches 88a and 88b at a time.

Now, the non-contact type switches need not always be installed on the surface of the microscope head 5, but a switch operating portion may be provided discretely near the microscope head 5, as shown in FIG. 8(B). For example, non-contact type switches may be disposed on a planar panel type switch board and may be mounted in a removable manner. Also, a system may be adopted in which the panel operating signal of the panel type switch board is transmitted to an electric motor control circuit by an FM wave, an optical signal or the like, whereby the switch board may be made wireless.

According to the present embodiment, non-contact type switches are used and thus, operation becomes simple and also infection can be prevented.

Figure 12:
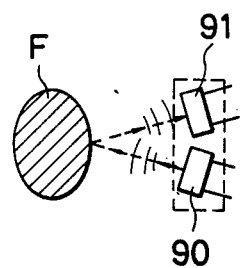
FIG. 12 illustrates a non-contact switch using ultrasonic wave.

In the embodiments described hitherto, reflection type photoswitches are used as the non-contact type switches, but alternatively, these may be transmission type photoswitches. The non-contact type switches are not limited to photoelectric type photoswitches, but may also be ultrasonic wave type non-contact switches which detect the approach of the finger tip by an ultrasonic wave transmitted 90 and an ultrasonic wave receiver 91 as shown in FIG. 12. As a further alternative, use may be made of non-contact type switches using well-known electrostatic capacity type sensors or of high frequency oscillation type proximity switches.

The above embodiments have been described with respect to a case where the device of the present invention is applied to a microscope for operation, whereas the present invention is not restricted to the microscope for operation, but is also applicable to ophthalmic instruments such as a keratometer and a refractometer, other medical instruments, general industrial instruments and general research instruments.

We claim:

1. A stereoscopic microscope, comprising:
   a plurality of driving means for driving means for performing a plurality of functions of said microscope, respectively;
   a plurality of first switches respectively provided for each driving means for remotely controlling said plurality of driving means;
   a second switch for detecting a specific selected driving means corresponding to a selected first switch before actual operation of said selected first switch; and
   transmitting means for transmitting information of said specific selected driving means to an operator.

2. A stereoscopic microscope according to claim 1, wherein said transmitting means is an indication device which displays the information of said specific selected driving means into a field of view of said microscope.

3. A stereoscopic microscope according to claim 1, wherein said transmitting means is a voice generator which transmits the information of said specific selected driving means to the operator as an audible voice signal.

4. A stereoscopic microscope according to claim 1, wherein said second switch is disposed in the vicinity of said corresponding selected first switch.

5. A stereoscopic microscope according to claim 4, wherein said second switch is a non-contact switch which detects an approximation of a predetermined object.

6. A stereoscopic microscope according to claim 1, wherein said second switch is disposed with said corresponding selected first switch in a body.

7. A stereoscopic microscope according to claim 6, wherein said second switch is a contact switch disposed on said plurality of first switches.

8. A stereoscopic microscope according to claim 6, wherein said plurality of first switches and said second switch are combined as a two-stroke switch which causes said second switch to assume an on-state at the first stroke thereof and which causes said plurality of first switches the assume an on-state at the second stroke thereof.

9. A stereoscopic microscope according to claim 1, wherein a driving state of said specific selected driving means is also transmitted to the operator during the driving of said specific selected driving means.

10. A stereoscopic microscope according to claim 9, wherein the driving state of said specific selected driving means drives said means performing a plurality of functions in a driving direction.

11. A stereoscopic microscope, comprising:
    a plurality of driving means for respectively driving means for performing a plurality of functions of said microscope;
    mode selecting means for arbitrarily selecting a driving means from said plurality of driving means;
    a multifunction switch combined with said mode selecting means for remotely operating said selected driving means; and
    transmitting means for transmitting information of said selected driving means to an operator.

12. A stereoscopic microscope according to claim 11, wherein said mode selecting means is a momentary switch.

13. A stereoscopic microscope according to claim 11, wherein said mode selecting switch is a voice switch which changes the mode of said mode selecting means in response to the operator's voice.

14. A stereoscopic microscope according to claim 11, wherein said mode selecting means and said multifunction switch are both non-contract switches.

15. A stereoscopic microscope according to claim 14, wherein said switches are mounted on a stereoscopic microscope head.

16. A stereoscopic microscope according to claim 14, wherein said switches are mounted in the vicinity of a stereoscopic microscope head.

17. A stereoscopic microscope according to claim 11, wherein said transmitting means is an indication device which displays the information of said selected driving means in a field of view of said microscope.

18. A stereoscopic microscope according to claim 11, wherein said transmitting means is a voice generator which transmits the information of said selected driving means to the operator as an audible voice signal.

19. A stereoscopic microscope according to claim 11, wherein a driving state of said selected driving means is also transmitted to the operator during the driving of said selected driving means.

20. A stereoscopic microscope according to claim 11, wherein the driving state of said selected driving means drives said means for performing a plurality of functions in a driving direction.

21. A stereoscopic microscope, comprising:

a plurality of driving means for driving means for performing a plurality of functions of said microscope, respectively;

a first switch for remotely driving said plurality of driving means;

a second switch for detecting a specific driving means which will be driven by said first switch before actual operation of said first switch; and transmitting means for transmitting information of said specific driving means selected by said second switch to an operator.

* * * * *

UNITED STATES PATENT AND TRADEMARK OFFICE
CERTIFICATE OF CORRECTION

PATENT NO. : 4,912,388
DATED : March 27, 1990
INVENTOR(S) : Tanaka, et al.

It is certified that error appears in the above-identified patent and that said Letters Patent is hereby corrected as shown below:

COLUMN 1:

Line 32, "Affixed strut 2" should read
            --A fixed strut 2--.

COLUMN 2:

Line 66, "focusing witch 10" should read
            --focusing switch 10--.

COLUMN 4:

Line 7, "200M" should read --ZOOM--.

COLUMN 5:

Line 68, "drives" should read --drives of the apparatus
            are connected to the motor driving--.

COLUMN 8:

Line 44, "mode hanging-over photoswitch," should read
            --mode changing-over photoswitch,--.

COLUMN 9:

Line 35, "transmitted 90" should read --transmitter 90--.

UNITED STATES PATENT AND TRADEMARK OFFICE
CERTIFICATE OF CORRECTION

PATENT NO. : 4,912,388
DATED : March 27, 1990
INVENTOR(S) : Tanaka, et al.

It is certified that error appears in the above-identified patent and that said Letters Patent is hereby corrected as shown below:

COLUMN 10:

Line 21, "the" should read --to--.

Line 52, "non-contract switches." should read --non-contact switches.--.

Signed and Sealed this

Seventh Day of April, 1992

Attest:

HARRY F. MANBECK, JR.

Attesting Officer     Commissioner of Patents and Trademarks